(12) United States Patent
Shturman

(10) Patent No.: US 8,157,825 B2
(45) Date of Patent: Apr. 17, 2012

(54) ATHERECTOMY DEVICE SUPPORTED BY FLUID BEARINGS

(75) Inventor: Leonid Shturman, Nyon (CH)

(73) Assignee: Lela Nadirashvili, Nyon (CH)

( * ) Notice: Subject to any disclaimer, the term of this patent is extended or adjusted under 35 U.S.C. 154(b) by 44 days.

(21) Appl. No.: 12/373,461

(22) PCT Filed: Jun. 28, 2007

(86) PCT No.: PCT/EP2007/056499
§ 371 (c)(1),
(2), (4) Date: Jan. 12, 2009

(87) PCT Pub. No.: WO2008/006704
PCT Pub. Date: Jan. 17, 2008

(65) Prior Publication Data
US 2009/0312777 A1    Dec. 17, 2009

(30) Foreign Application Priority Data
Jul. 13, 2006  (GB) .................................. 0613979.4

(51) Int. Cl.
*A61B 17/22*  (2006.01)
(52) U.S. Cl. .......................................... 606/159; 604/22
(58) Field of Classification Search ............ 606/110, 606/112, 114, 127, 128, 170, 180, 191, 15; 604/22, 103.01, 103.02
See application file for complete search history.

(56) References Cited

U.S. PATENT DOCUMENTS

| 1,431,416 | A | 10/1922 | Parsons et al. |
| 1,916,085 | A | 6/1933 | Summers et al. |
| 4,646,736 | A | 3/1987 | Auth |
| 4,870,953 | A | 10/1989 | DonMicheal et al. |
| 4,931,635 | A | 6/1990 | Toyama |
| 4,990,134 | A | 2/1991 | Auth |
| 5,100,425 | A | 3/1992 | Fischell et al. |

(Continued)

FOREIGN PATENT DOCUMENTS

EP    0419154    3/1991

(Continued)

OTHER PUBLICATIONS

International Search Report, corresponding to Int'l Application No. PCT/EP2007/056499 (dated Oct. 23, 2007).

(Continued)

*Primary Examiner* — Tuan Nguyen
*Assistant Examiner* — David Eastwood
(74) *Attorney, Agent, or Firm* — Fish & Richardson P.C.

(57) ABSTRACT

A rotational atherectomy device for removing a stenotic tissue (330, 360) from a vessel (300) of a patient comprises a flexible hollow drive shaft (2) and an abrasive element (101, 102) mounted to the drive shaft proximal to and spaced from a solid support element (10, 10s) mounted at the distal end (6) of the drive shaft, the solid support element having a rounded outer surface and an outflow channel (20, 20s) with an outflow opening in said rounded outer surface. The drive shaft comprises a torque transmitting coil (4) and at least one fluid impermeable membrane (3) forming a fluid impermeable lumen for the antegrade flow (FF) of fluid into the outflow channel such that, during rotation of the drive shaft, a flow of fluid out of said outflow opening forms a fluid bearing between the rotating solid support element and the wall of the treated vessel.

9 Claims, 4 Drawing Sheets

U.S. PATENT DOCUMENTS

| | | | |
|---|---|---|---|
| 5,217,474 A | 6/1993 | Zacca et al. | |
| 5,242,460 A | 9/1993 | Klein et al. | |
| 5,250,060 A | 10/1993 | Carbo et al. | |
| 5,273,526 A | 12/1993 | Dance | |
| 5,308,354 A | 5/1994 | Zacca et al. | |
| 5,314,438 A | 5/1994 | Shturman | |
| 5,342,292 A | 8/1994 | Nita et al. | |
| 5,361,285 A | 11/1994 | Formanek et al. | |
| 5,370,653 A | 12/1994 | Cragg | |
| 5,458,575 A | 10/1995 | Wang | |
| 5,584,843 A * | 12/1996 | Wulfman et al. | 606/159 |
| 5,681,336 A * | 10/1997 | Clement et al. | 606/159 |
| 5,843,103 A | 12/1998 | Wulfman | |
| 5,868,708 A | 2/1999 | Hart et al. | |
| 6,010,533 A | 1/2000 | Pope et al. | |
| 6,096,054 A | 8/2000 | Wyzgala et al. | |
| 6,132,444 A | 10/2000 | Shturman et al. | |
| 6,135,982 A | 10/2000 | Campbell | |
| 6,146,395 A | 11/2000 | Kanz et al. | |
| 6,152,911 A | 11/2000 | Giannoble | |
| 6,156,048 A | 12/2000 | Wulfman et al. | |
| 6,241,706 B1 | 6/2001 | Leschinsky et al. | |
| 6,270,465 B1 | 8/2001 | Keith et al. | |
| 6,416,526 B1 | 7/2002 | Wyzgala et al. | |
| 6,485,500 B1 | 11/2002 | Kokish et al. | |
| 6,491,660 B2 | 12/2002 | Guo et al. | |
| 6,685,718 B1 | 2/2004 | Wyzgala et al. | |
| 6,955,661 B1 | 10/2005 | Herweck et al. | |
| 2002/0007190 A1 * | 1/2002 | Wulfman et al. | 606/167 |
| 2002/0082547 A1 | 6/2002 | Deniega et al. | |
| 2002/0099367 A1 * | 7/2002 | Guo et al. | 606/43 |
| 2002/0138088 A1 | 9/2002 | Nash et al. | |
| 2002/0188276 A1 | 12/2002 | Evans et al. | |
| 2003/0199889 A1 | 10/2003 | Kanz et al. | |
| 2004/0098014 A1 | 5/2004 | Flugelman et al. | |
| 2004/0158270 A1 | 8/2004 | Wyzgala et al. | |
| 2005/0154416 A1 | 7/2005 | Herweck et al. | |
| 2005/0209615 A1 * | 9/2005 | Prudnikov et al. | 606/159 |
| 2005/0240146 A1 | 10/2005 | Nash et al. | |
| 2005/0256461 A1 | 11/2005 | DiFiore et al. | |

FOREIGN PATENT DOCUMENTS

| | | |
|---|---|---|
| WO | WO 98/50101 | 11/1998 |
| WO | WO 9944513 A2 | 9/1999 |
| WO | WO 0209599 | 2/2002 |
| WO | WO 2006126076 A2 | 11/2006 |
| WO | WO 2006126175 A2 | 11/2006 |
| WO | WO 2006126176 A1 | 11/2006 |

OTHER PUBLICATIONS

Declaration of Aleksey Filippov, Apr. 23, 2007, 1 page.
Declaration of Dmitri Prudnikov, Apr. 23, 2007, 1 page.
Excerpt from Deposition of Dmitri Prudnikov, Mar. 5, 2008, 7 pages.
Excerpt from Deposition of Dmitri Prudnikov, Mar. 6, 2008, 54 pages.
Exhibits Nos. 14, 31 & 32, from Deposition of Dmitri Prudnikov, Mar. 5, 2008, 3 pages.
Exhibits Nos. 33-39 from Deposition of Dmitri Prudnikov, Mar. 6, 2008, 47 pages.

* cited by examiner

ATHERECTOMY DEVICE SUPPORTED BY FLUID BEARINGS

CROSS-REFERENCE TO RELATED APPLICATIONS

This application is a national phase application based on PCT/EP2007/056499, filed Jun. 28, 2007, the content of which is incorporated herein by reference, and claims priority of GB Patent Application No. 0613979.4, filed Jul. 13, 2006, the content of which is incorporated by herein by reference.

BACKGROUND OF THE INVENTION

1. Field

The present invention provides a rotational atherectomy device for removing a stenotic lesion from within a vessel of a patient. More specifically, the invention relates to a rotational atherectomy device for removing or reducing stenotic lesions in blood vessels such as a human artery by rotating an abrasive element within the vessel to partially or completely ablate the unwanted material.

2. Description of the Related Art

Atherosclerosis, the clogging of arteries, is a leading cause of coronary heart disease. Blood flow through the peripheral arteries (e.g., carotid, femoral, renal, etc.), is similarly affected by the development of atherosclerotic blockages. A conventional method of removing or reducing blockages in blood vessels is known as totational atherectomy. A long guidewire is advanced into the diseased blood vessel and across the stenotic lesion. A hollow drive shaft is then advanced over the guidewire. The distal end of the drive shaft terminates in a burr provided with an abrasive surface formed from diamond grit or diamond particles. The burr is positioned against the occlusion and the drive shaft rotated at extremely high speeds (e.g., 20,000-160,000 rpm). As the burr rotates, the physician slowly advances it so that the abrasive surface of the burr scrapes against the occluding tissue and disintegrates it, reducing the occlusion and improving the blood flow through the vessel. Such a method and a device for performing the method are described in, for example, U.S. Pat. No. 4,990,134 to Auth. It is also known from U.S. Pat. No. 6,132,444 to Shturman (the instant inventor) et al., to provide a drive shaft with an abrasive element eccentrically positioned proximally to and spaced away from the distal end of the drive shaft.

Rotational angioplasty (atherectomy) is frequently used to remove atherosclerotic or other blocking material from stenotic (blocked) coronary arteries and other blood vessels. However, a disadvantage with this technique is that abraded particles can migrate along the blood vessel distally and block very small diameter vessels including capillaries of the heart muscle itself. The effect of the particulate debris produced by this procedure is of major concern to physicians who practice in this field. Clearly, the existence of particulate matter in the blood stream is undesirable and can cause potentially life-threatening complications, especially if the particles are over a certain size.

Although the potentially detrimental effect caused by the presence of abraded particles in the blood vessels is reduced if they are very small microparticles, it is much more preferable to remove from the treated blood vessel any debris abraded or otherwise released from the stenotic lesion during treatment and thereby prevent migration of debris to other locations along the treated blood vessel.

A rotational atherectomy device, described in U.S. Pat. No. 5,681,336 (to Clement et al.), has been proposed which attempts to prevent migration of abraded particles along the blood stream by removing the ablated material from the blood vessel whilst the device is in use. The rotational atherectomy device known from U.S. Pat. No. 5,681,336 (to Clement et al.) has a complicated construction and is difficult to manufacture on a commercial scale.

A number of disadvantages associated with the known rotational atherectomy devices have been addressed in WO 2006/126076, WO 2006/126175 and WO 2006/126176 to Shturman (the instant inventor). The present invention seeks to further improve rotational atherectomy devices known from these documents and other disadvantages associated with known atherectomy devices.

Two most preferred embodiments of the Rotational Atherectomy Device with Solid Support Elements are described in WO 2006/126076. Both embodiments comprise an abrasive element and a pair of solid support elements mounted to a hollow drive shaft formed from a torque transmitting coil and a fluid impermeable membrane. In both preferred embodiments, the abrasive element is located proximal to and spaced away from the distal end. The solid support elements described in WO 2006/126076 are rounded. One of them is located at the distal end of the drive shaft and is referred to as the distal solid support element. The other is located proximal to and spaced away from the abrasive element and is referred to as the proximal distal support element.

In one embodiment of the invention described in WO 2006/126076, the abrasive element has its centre of mass spaced away from the longitudinal or rotational axis of the drive shaft. In that embodiment, both the distal and the proximal solid support elements also have their centres of mass spaced radially away from the longitudinal or rotational axis of the drive shaft, the centre of mass of each of the two solid support elements being located diametrically opposite to the centre of mass of the abrasive element with respect to the longitudinal axis of the drive shaft so that the distal and proximal solid support elements act as counterweights with respect to the abrasive element when the drive shaft rotates. Most preferably, the distal and proximal solid support elements are located in the same longitudinal plane as the centre of mass of the abrasive element, the longitudinal plane extending through the longitudinal or rotational axis of the drive shaft.

In another embodiment described in WO 2006/126076, the abrasive element and the solid support elements have their centres of mass coaxial with the longitudinal or rotational axis of the fluid impermeable drive shaft.

In both embodiments described in WO 2006/126076, pressurised fluid enters treated vessel only through a distal end opening of the fluid impermeable lumen of the drive shaft.

SUMMARY

According to the invention, there is provided a rotational atherectomy device for removing a stenotic tissue from a vessel of a patient, the device comprising a rotatable, flexible, hollow drive shaft having a distal end, an abrasive element mounted to the drive shaft proximal to and spaced away from a distal solid support element mounted at the distal end of the drive shaft, the distal solid support element having a rounded outer surface and comprising an outflow channel extending through the solid distal support element, the outflow channel having an outflow opening in said rounded outer surface, the drive shaft comprising a torque transmitting coil and at least one fluid impermeable membrane forming a fluid impermeable lumen for the antegrade flow of fluid along the torque transmitting coil into the outflow channel of the solid distal support element such that, during rotation of the drive shaft, said outflow opening of the outflow channel is facing an inner surface of a vessel being treated so that a flow of fluid out of said outflow opening forms a layer of fluid between the solid distal support element and a wall of the treated vessel, said layer of fluid forming a fluid bearing between the rotating solid distal support element and the wall of the treated vessel.

In a preferred embodiment, the fluid impermeable drive shaft is provided with a solid proximal support element located proximal to and spaced away from the abrasive element, the membrane that forms a fluid impermeable lumen for the antegrade flow of fluid along the torque transmitting coil into the outflow channel of the distal solid support element also forming a lumen for the antegrade flow of fluid along the torque transmitting coil into an outflow channel extending through said solid proximal support element, the solid proximal support element having a rounded outer surface, said outflow channel having an outflow opening in the rounded outer surface of the solid proximal support element such that, during rotation of the drive shaft, said outflow opening on the outer surface of the solid proximal support element is facing an inner surface of a treated vessel so that a flow of fluid out of said outflow opening forms a layer of fluid between the solid proximal support element and a wall of the treated vessel, said layer of fluid forming a fluid bearing between the rotating solid proximal support element and the wall of the treated vessel.

In one embodiment, the drive shaft preferably has a longitudinal axis and the solid distal support element has a centre of mass which is coaxial with the longitudinal axis of the drive shaft, said distal support element having a plurality of outflow channels that extend through the distal support element in a radially outward direction with respect to the longitudinal axis of the drive shaft and have their outflow openings spaced around the circumference of the solid distal support element such that, during rotation of the drive shaft, a flow of fluid through the outflow openings forms a layer of fluid between the solid distal support element and a wall of the vessel being treated, said layer of fluid forming a fluid bearing between the rotating solid distal support element and the wall of the vessel being treated. In this embodiment, the centre of mass of the abrasive element may either be coaxial with the longitudinal axis of the drive shaft or, spaced radially away from the longitudinal axis of the drive shaft.

In an embodiment where there is a solid proximal support element, the solid proximal support element may have a centre of mass coaxial with the longitudinal axis of the drive shaft, said proximal support element having a plurality of outflow channels extending through the solid proximal support element in a radially outward direction with respect to the longitudinal axis of the drive shaft and having their outflow openings located around the circumference of the solid proximal support element such that, during rotation of the drive shaft, a flow of fluid out of the outflow openings forms a layer of fluid between the solid proximal support element and a wall of the vessel being treated, said layer of fluid forming a fluid bearing between the rotating solid proximal support element and the wall of the vessel being treated. In this embodiment, the centre of mass of the abrasive element may either be coaxial with the longitudinal axis of the drive shaft or, spaced radially away from the longitudinal axis of the drive shaft.

In one embodiment, the solid distal support element may have its centre of mass spaced radially away from the longitudinal axis of the drive shaft in one direction so that it acts as a counterweight to the abrasive element, which has its centre of mass spaced radially away from the longitudinal axis of the drive shaft in a diametrically opposite direction.

In an embodiment in which the abrasive element has its centre of mass spaced radially away from a longitudinal axis of the drive shaft, the centres of mass of both distal and proximal solid support elements may be spaced radially away from a longitudinal axis of the drive shaft but in a direction diametrically opposite to the direction in which the abrasive element is spaced radially away from the longitudinal axis of the drive shaft so that the distal and proximal solid support elements act as counterweights to the abrasive element.

It will be appreciated that there may be a plurality of outflow channels in the solid distal support element in any of the embodiments of the invention.

It should be emphasized that the present invention covers two most preferred embodiments in one of which the solid support elements are asymmetrical with respect to the longitudinal axis of the drive shaft. In the other preferred embodiment, the solid support elements are symmetric with respect to the longitudinal axis of the drive shaft. However, it will be appreciated that, in all the embodiments, the asymmetric and symmetric solid support elements comprise outflow channels located such that, in the rotating drive shaft, fluid flowing out of said channels forms fluid bearings between outer walls of said solid support elements and the wall of the treated vessel.

It should be noted that throughout this specification, reference is made to "distal" and "proximal" ends and to flow of fluid in an "antegrade" and "retrograde" direction. For the avoidance of doubt, the distal end is considered to refer to the end of the device which is inserted into the vessel in the body of the patient and the proximal end is the end of the device which remains outside the body of the patient and which can be connected to a handle assembly for both rotating and longitudinally moving the drive shaft within the treated vessel. "Antegrade" flow refers to a direction of flow from the proximal towards the distal end of the device. Similarly, "retrograde" flow refers to a direction of flow in the opposite direction, i.e. from the distal towards the proximal end of the device.

BRIEF DESCRIPTION OF THE DRAWINGS

Embodiments of the invention will now be described, by way of example only, and with reference to the accompanying drawings, in which.

DETAILED DESCRIPTION

Figure 1:
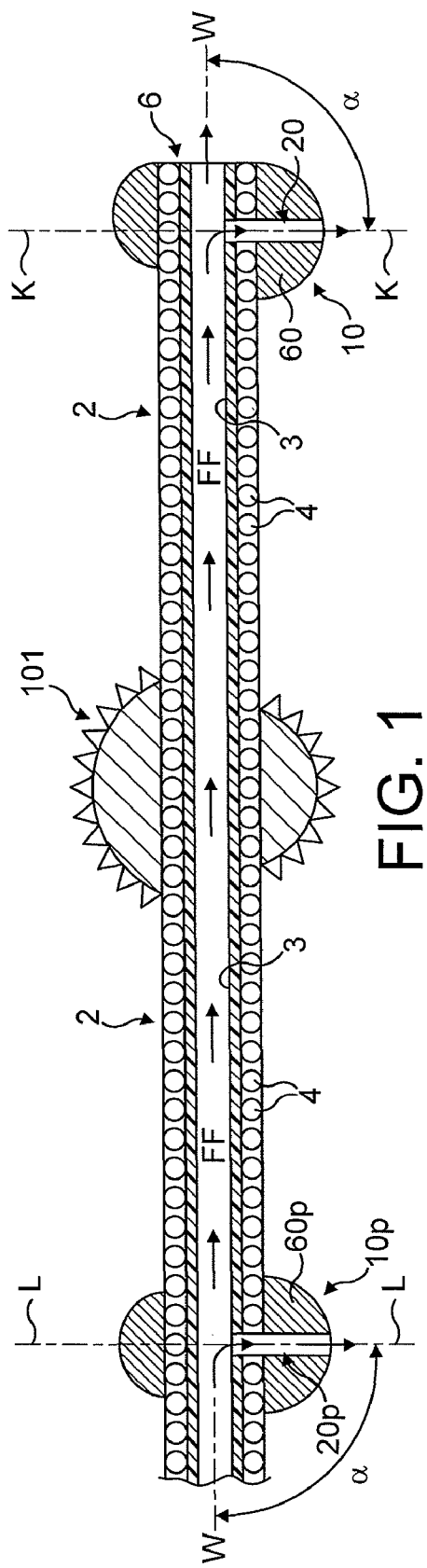
FIG. 1 illustrates in a longitudinal cross-section a distal portion of one preferred embodiment of the rotational atherectomy device of the invention, this embodiment comprising asymmetric solid support elements and illustrating the location of outflow channels which extend through said solid support elements.

In FIGS. 1 to 4, the antegrade flow of fluid is indicated by arrows "FF" and the flow of fluid in a retrograde direction is indicated by arrows marked "R". Abraded particles AP abraded from the stenotic lesion 330 are aspirated into a lumen of a drive shaft sheath 400 so that the retrograde flowing fluid and the abraded particles entrained in said fluid can be removed from the treated vessel and out of the patient's body.

Referring to the drawings, there is shown a rotational atherectomy device for removing a stenotic lesion from within a vessel of a patient using an abrasive element mounted to a rotatable, flexible, hollow drive shaft formed by a torque transmitting coil and a fluid impermeable membrane. The drive shaft has a longitudinal axis of rotation and is provided with two rounded solid support elements. Each of the two solid support elements is spaced away from the abrasive element and includes at least one outflow channel which is directed radially outward and communicates a lumen of the drive shaft with a vascular space of the treated vessel, one of said solid support elements is a distal solid support element and is located at a distal end of the drive shaft and the other is a proximal solid support element and is located proximal to the abrasive element.

In a preferred embodiment, each of the distal and proximal solid support elements has a rounded surface and is spaced equally from the abrasive element which extends around the entire circumference of the drive shaft.

In one embodiment of the invention the abrasive element and each of the two solid support elements are symmetric with respect to the rotational (longitudinal) axis of the drive shaft. In another embodiment of the invention the abrasive element and the solid support elements have their centres of mass spaced radially away from the rotational Longitudinal) axis of the drive shaft.

Each outflow channel has its own axis and each of the solid support elements has at least one outflow channel located such that its axis comprises an acute angle of at least seventy five (75) degrees with the longitudinal (rotational) axis of the drive shaft. In a preferred embodiment each of the solid support elements has at least one outflow channel located such that its axis comprises an angle of about (90) degrees with the longitudinal (rotational) axis of the drive shaft. In the most preferred embodiment of the invention each of the symmetric solid support elements has at least a few outflow channels equally spaced around the maximum circumference of the support element, each of said outflow channels having an axis which comprises an angle of about ninety (90) degrees with the longitudinal (rotational) axis of the drive shaft. In any of the preferred embodiments of the invention at least one outflow channel is located such that in a rotating drive shaft fluid which flows through the outflow channel along its axis forms at least a thin layer of fluid between the solid support element and the wall of the treated vessel.

FIG. 1 illustrates, in a longitudinal cross-section, a distal portion of one preferred embodiment of the rotational atherectomy device of an embodiment of the invention. The rotational atherectomy device is comprised of an asymmetric abrasive element 101 which extends around the entire circumference of the drive shaft 2 proximal to and spaced away from a distal end 6 of the drive shaft. The fluid impermeable drive shaft 2 is comprised by a fluid impermeable membrane 3 which lines a torque transmitting coil 4. Both the torque transmitting coil 4 and the fluid impermeable membrane 3 extend distally beyond the abrasive element 101.

FIG. 1 illustrates an asymmetric distal support element 10 which has its centre of mass spaced radially away from the longitudinal (rotational) axis W-W of the drive shaft 2. The Figure illustrates that at least one outflow channel 20 which extends through a heavier portion 60 of the asymmetric distal support element 10, the axis K-K of the outflow channel 20 comprises an acute angle α of about ninety (90) degrees with the longitudinal (rotational) axis W-W of the drive shaft. However, it will be appreciated that there may be a plurality of outflow channels 20 and the axes of these channels may form an acute angle of up to 30 degrees with axis K-K of the most important outflow channel. Its axis K-K being oriented perpendicular to the longitudinal axis of the drive shaft. In the most preferred embodiment of the invention, axis K-K of at least one outflow channel 20 passes through or close to the centre of mass of the asymmetric distal solid support element.

Figure 2:
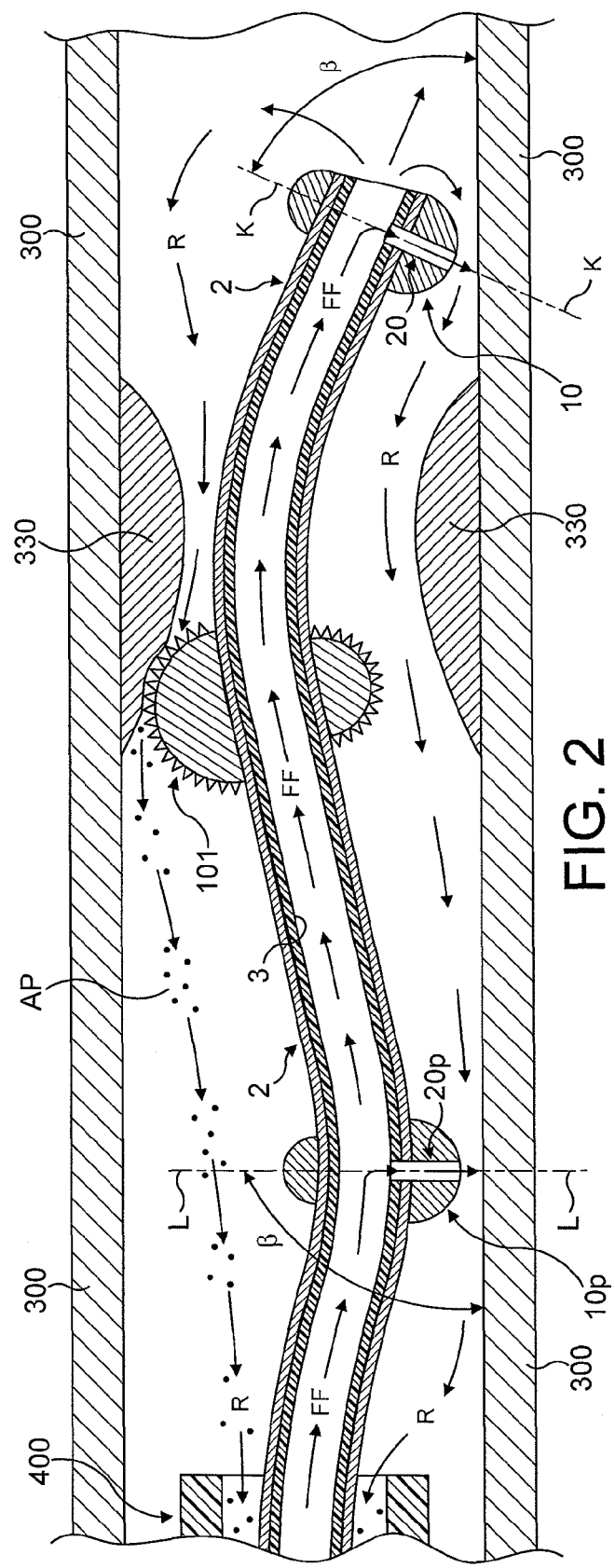
FIG. 2 illustrates the device of FIG. 1 located in a vessel being treated and shows how the device can be used to abrade a stenotic lesion while forming fluid bearings between rounded outer surfaces of asymmetric solid support elements located distal and proximal to the abrasive element.

FIGS. 1 and 2 illustrate that a portion of flushing fluid FF flowing in an antegrade direction through the drive shaft 2 is redirected through the outflow channel 20 into a vascular space of the treated vessel.

FIG. 2 illustrates that in a rotating drive shaft centrifugal force attempts to press a rotating asymmetric solid distal support element 10 against the wall 300 of the treated vessel but fluid exiting through the outflow channel 20 along its axis K-K and forms an acute angle β of over 75 degrees with an inner surface of a wall 300 of the treated vessel so that fluid flowing through the outflow channel 20 forms a thin layer of fluid between the solid support element 10 and an inner surface of the treated vessel. This thin layer of fluid acts as a fluid bearing between the asymmetric distal solid support element 10 and a wall 300 of the treated vessel. At least a portion of fluid flowing through the outflow channel 20 flows in a retrograde direction, as indicated by arrows marked "R", and entrains abraded particles AP removed from the stenotic lesion 330. The retrograde flowing flushing fluid R and entrained abraded particles AP are aspirated into a lumen of the drive shaft sheath 400.

FIG. 1 illustrates an asymmetric proximal support element 10p which has its centre of mass spaced radially away from the longitudinal (rotational) axis W-W of the drive shaft 2. The Figure illustrates that at least one outflow channel 20p extends through a heavier portion 60p of the asymmetric proximal support element 10p. The outflow channel 20p has an axis L-L which forms an acute angle α of about ninety (90) degrees with the longitudinal (rotational) axis W-W of the drive shaft. However, it will be appreciated that there may be a plurality of outflow channels 20p and the axes of these channels may form an acute angle of up to 30 degrees with axis L-L of the most important outflow channel that has its axis L-L oriented perpendicular to the longitudinal axis of the drive shaft.

FIGS. 1 and 2 illustrate that a portion of flushing fluid FF flowing in an antegrade direction through the drive shaft 2 is redirected through the outflow channel 20p into a vascular space of the treated vessel.

FIG. 2 illustrates that in a rotating drive shaft centrifugal force attempts to press a rotating asymmetric solid proximal support element 10p against the wall 300 of the treated vessel but fluid exiting through the outflow channel 20p along its axis L-L forms an angle β of about ninety (90) degrees with an inner surface of a wall 300 of the treated vessel so that fluid flowing through the outflow channel 20p forms a thin layer of fluid between the solid support element 10p and an inner surface of the treated vessel. This thin layer of fluid acts as a fluid bearing between the asymmetric distal solid support element 10p and a wall 300 of the treated vessel.

Figure 3:
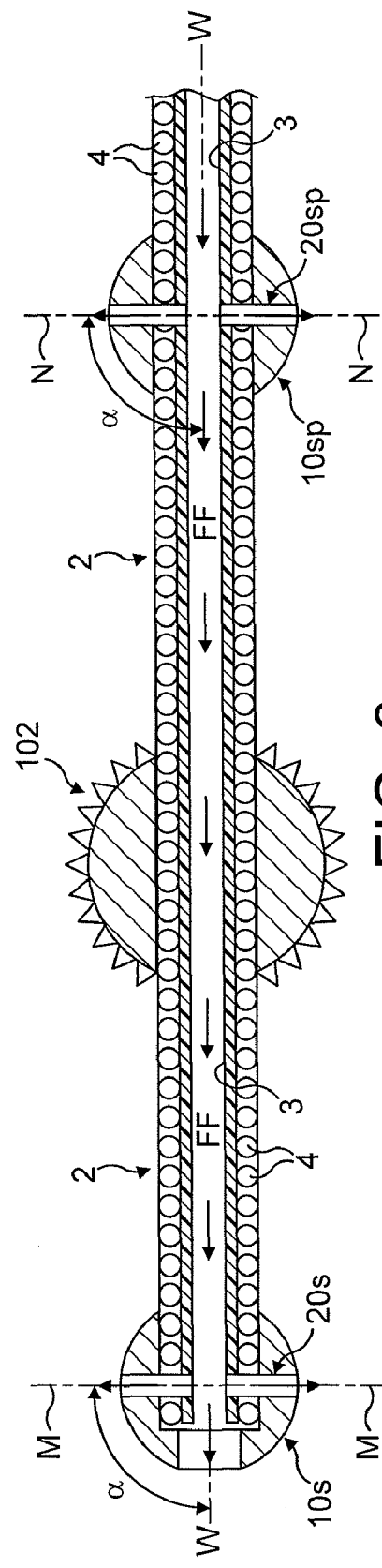
FIG. 3 illustrates in a longitudinal cross-section a distal portion of one preferred embodiment of the rotational atherectomy device of the invention, this embodiment comprising symmetric solid support elements located distal and proximal to the symmetric abrasive element and illustrates location of outflow channels which extend through said solid support elements.

FIG. 3 illustrates a symmetric distal support element 10s. The centre of mass of the symmetric distal support element 10s coincides with the longitudinal (rotational) axis W-W of the drive shaft 2. In a preferred embodiment of the invention at least a few outflow channels 20s should extend radially outward through the symmetric distal support element 10s communicating a fluid impermeable lumen of the drive shaft 2 with a vascular space of the treated vessel. Preferably said outflow channels 20s should be equally spaced around the maximum diameter circumference of the symmetric distal solid support element 20s. FIG. 3 illustrates that an axis M-M of at least one outflow channel 20s comprises an acute angle of over seventy five (75) degrees with the longitudinal (rotational) axis W-W of the drive shaft 2. In the preferred embodiment axis M-M of the outflow channel 20s forms an angle α of about ninety (90) degrees with the longitudinal (rotational) axis W-W of the drive shaft.

Figure 4:
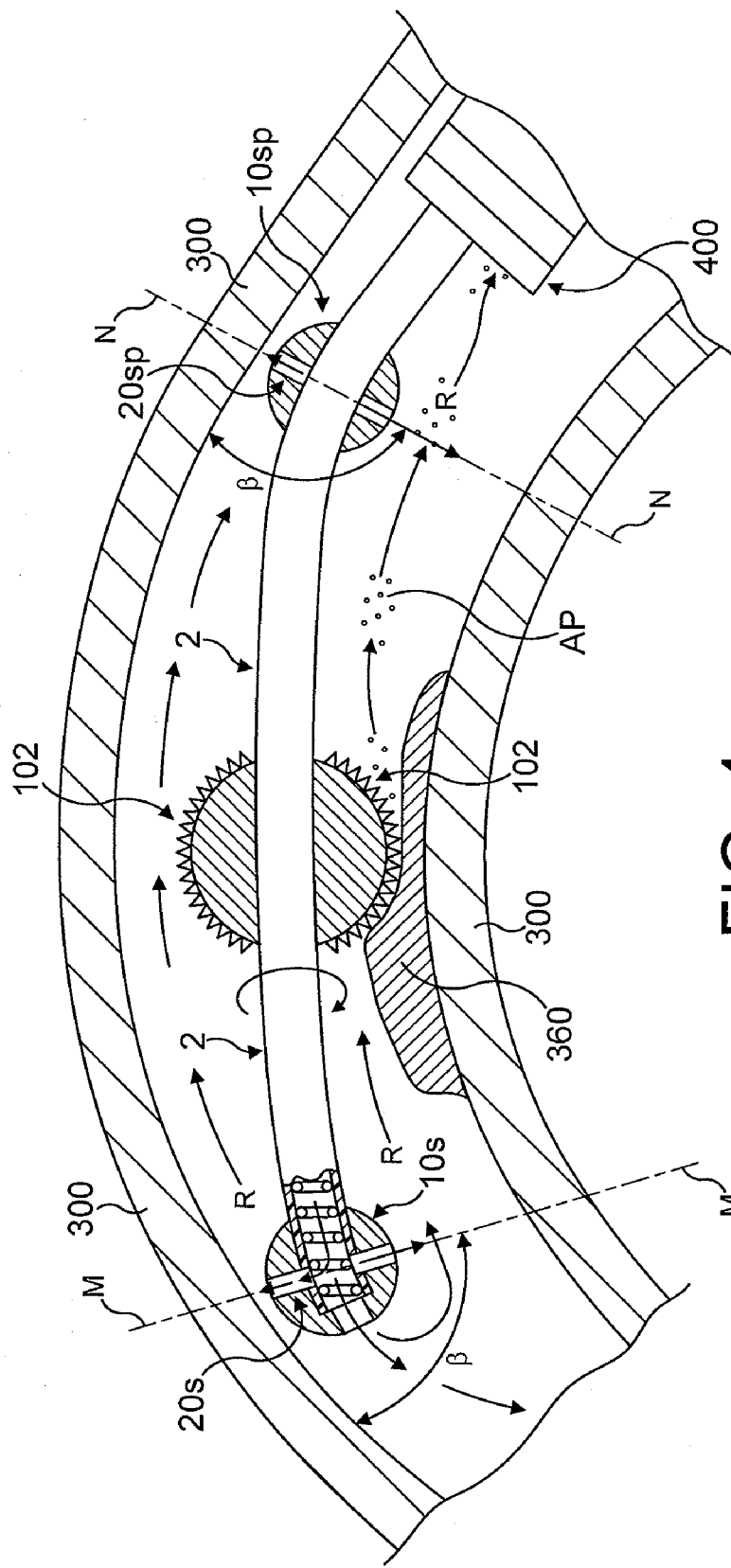
FIG. 4 illustrates the device of FIG. 3 located in a vessel being treated and shows how the device can be used to abrade a stenotic lesion in a curved vessel. This Figure also shows how fluid bearings are formed between the rounded outer surfaces of symmetric solid support elements and the wall of the treated vessel.

FIGS. 3 and 4 illustrate that a portion of flushing fluid FF flowing in an antegrade direction through the drive shaft 2 is redirected through the outflow channels 20s into a vascular space of the treated vessel.

FIG. 4 illustrates that, in a curved vessel, the drive shaft 2 attempts to maintain its straight configuration and therefore attempts to press both of the solid symmetric support elements towards the outer curvature of the vessel and the symmetric abrasive element 102 towards the inner curvature of the vessel.

FIG. 4 illustrates that in a rotating drive shaft the axis M-M of the outflow channel 20s forms an angle β of about ninety (90) degrees with an inner surface of a wall 300 of the treated vessel so that fluid flowing through the outflow channel 20s along its axis M-M forms a thin layer of fluid between the solid support element 10s and an inner surface of the treated vessel. This thin layer of fluid acts as a fluid bearing between the solid support element 10s and a wall 300 of the treated vessel. At least a portion of the fluid flowing through the outflow channels 20 is flowing in a retrograde direction R and entrains abraded particles AP removed (abraded) by the symmetric abrasive element 102 from the stenotic lesion 360 located on the inner curvature of the vessel 300. The retrograde flowing flushing fluid R is aspirated into a lumen of the drive shaft sheath 400.

FIG. 3 illustrates a symmetric proximal support element 10sp. The centre of mass of the symmetric proximal support element 10sp coincides with the longitudinal (rotational) axis of the drive shaft 2. In a preferred embodiment of the invention at least a few outflow channels 20sp should extend radially outward through the symmetric proximal support element 10sp communicating a fluid impermeable lumen of the drive shaft 2 with a vascular space of the treated vessel. Preferably said outflow channels 20sp should be equally spaced around the maximum diameter circumference of the symmetric distal solid support element 20sp. FIG. 3 illustrates that an axis N-N of at least one outflow channel 20sp comprises an acute angle of at least seventy five (75) degrees with the longitudinal (rotational) axis W-W of the drive shaft 2. In the preferred embodiment axis N-N of the outflow channels 20sp forms an angle α of about ninety (90) degrees with the longitudinal (rotational) axis W-W of the drive shaft. FIGS. 3 and 4 illustrate that a portion of flushing fluid FF flowing in an antegrade direction through the drive shaft 2 is redirected through the outflow channel 20sp into a vascular space of the treated vessel.

FIG. 4 illustrates that in a rotating drive shaft the axis N-N of the outflow channel 20sp forms an angle β of about ninety (90) degrees with an inner surface of a wall 300 of the treated vessel so that fluid flowing through the outflow channel 20sp along its axis N-N forms a thin layer of fluid between the proximal solid support element 10sp and an inner surface of the treated vessel. This thin layer of fluid acts as a fluid bearing between the proximal solid support element 10sp and a wall 300 of the treated vessel.

FIG. 3 illustrates an embodiment in which a fluid impermeable membrane lines the torque transmitting coil. In an alternative embodiment, illustrated in FIG. 4, the fluid impermeable membrane is disposed around the torque transmitting coil.

It will be appreciated that the device with symmetric support elements is not intended to be exclusively used in curved vessels but can also be used successfully in straight vessels.

Many modifications and variations of the invention falling within the terms of the following claims will be apparent to a person skilled in the art and the foregoing description should be regarded as a description of the preferred embodiments only.

The invention claimed is:

1. A rotational atherectomy device for removing a stenotic tissue from a vessel of a patient, the device comprising an abrasive element mounted to a rotatable, flexible, hollow drive shaft having a longitudinal axis and a distal end, the abrasive element being mounted to the drive shaft between a distal solid support element and a proximal solid support element, the abrasive element being positioned proximal to and spaced away from the distal solid support element which is mounted at the distal end of the drive shaft, and the abrasive element being positioned distal to and spaced away from the proximal solid support element, each of the distal and proximal solid support elements being substantially smaller than the abrasive element and having a surface texture that is different from an abrasive surface texture of the abrasive element, the drive shaft comprising a torque transmitting coil and at least one fluid impermeable membrane positioned radially inward of the torque transmitting coil to form a fluid impermeable lumen along a central longitudinal axis of the drive shaft for an antegrade flow of fluid through the drive shaft, the distal solid support element having a rounded outer surface and comprising an outflow channel which is in fluid communication with the fluid impermeable lumen of the drive shaft and which extends through the solid distal support element in a generally radially outward direction with respect to the longitudinal axis of the drive shaft, the outflow channel having an outflow opening in said rounded outer surface located such that, during rotation of the drive shaft, said outflow opening is configured to output fluid flow for forming a fluid layer between the solid distal support element and a wall of a vessel, said layer of fluid being operable to form a fluid bearing between the rotating solid distal support element and the wall of the vessel during rotation and back and forth movements of the drive shaft within the vessel, wherein said distal and proximal solid support elements are configured to act as counterweights to the abrasive element.

2. A rotational atherectomy device according to claim 1, wherein the solid proximal support element has a rounded outer surface and comprising an outflow channel which is in fluid communication with the fluid impermeable lumen of the drive shaft and which extends through the solid proximal support element in a generally radially outward direction with respect to the longitudinal axis of the drive shaft, the outflow channel having an outflow opening in said rounded outer surface of the solid proximal support element located such that, during rotation of the drive shaft, said outflow opening is configured to output fluid flow for forming a fluid layer between the solid proximal support element and the wall of the vessel, said layer of fluid being operable to form a fluid bearing between the rotating solid proximal support element and the wall of the vessel.

3. A rotational atherectomy device according to claim 2, wherein the abrasive element and each of the distal and proximal solid support elements have their individual centers of mass, the centers of mass of both the distal and proximal solid support elements being spaced radially away from a longitudinal axis of the drive shaft but in a direction diametrically opposite to the direction in which a center of mass of the abrasive element is spaced radially away from the longitudinal axis of the drive shaft so that the distal and proximal solid support elements act as counterweights to the abrasive element.

4. A rotational atherectomy device according to claim 1, wherein the fluid impermeable membrane lines the torque transmitting coil.

5. A rotational atherectomy device according to claim 1, wherein the fluid impermeable lumen of the drive shaft is configured for advancement of the drive shaft over a guidewire across a stenotic lesion to be treated and for transfer of pressurized fluid into the outflow channel of the distal solid support element after crossing the stenotic lesion.

6. A rotational atherectomy device for removing a stenotic lesion from within a vessel of a patient, the device comprising a rotatable, flexible, hollow drive shaft having a longitudinal axis of rotation and an abrasive element mounted proximal to and spaced away from a distal end of the drive shaft, the drive shaft including a distal solid support element located at the distal end of the drive shaft and spaced away from the abrasive element and including a proximal solid support element located proximal to and spaced away from the abrasive element, each of the distal and proximal solid support elements being substantially smaller than the abrasive element and having a surface texture that is different from an abrasive surface texture of the abrasive element, the drive shaft having a fluid impermeable wall defining a fluid impermeable lumen for an antegrade flow of fluid through the drive shaft, wherein both the distal and proximal solid support elements have an outflow channel that is in fluid communication with the fluid impermeable lumen of the drive shaft and extend through each of the support elements in a generally radially outward direction with respect to the longitudinal axis of the drive shaft, the outflow channels have axes that form angles of about ninety (90) degrees with the longitudinal axis of the drive shaft and have outflow openings along circumferences of the support elements such that, during rotation of the drive shaft, the outflow openings are configured to output fluid flow for forming layers of fluid between the solid support elements and a wall of the vessel, said layers of fluid being operable to form fluid bearings between the rotating solid support elements and the wall of the vessel during rotation and back and forth movements of the drive shaft within the vessel, wherein said distal and proximal solid support elements are configured to act as counterweights to the abrasive element.

7. A rotational atherectomy device according to claim 6, wherein the fluid impermeable lumen of the drive shaft is configured for advancement of the drive shaft over a guidewire across a stenotic lesion to be treated and for transfer of pressurized fluid into the outflow channels of both the distal and proximal solid support elements after crossing the stenotic lesion.

8. A rotational atherectomy device according to claim 6, wherein the abrasive element and each of the distal and proximal solid support elements have their individual centers of mass, the centers of mass of both the distal and proximal solid support elements being spaced radially away from the longitudinal axis of the drive shaft but in a direction diametrically opposite to the direction in which a center of mass of the abrasive element is spaced radially away from the longitudinal axis of the drive shaft so that the distal and proximal solid support elements act as counterweights to the abrasive element.

9. A rotational atherectomy device according to claim 6, wherein the fluid impermeable wall lines the torque transmitting coil.

* * * * *